(12) United States Patent
Pisharodi

(10) Patent No.: US 7,074,240 B2
(45) Date of Patent: Jul. 11, 2006

(54) METHOD AND APPARATUS FOR STABILIZING ADJACENT VERTEBRAE

(75) Inventor: Madhavan Pisharodi, Brownsville, TX (US)

(73) Assignee: Perumala Corporation, Brownsville, TX (US)

( * ) Notice: Subject to any disclaimer, the term of this patent is extended or adjusted under 35 U.S.C. 154(b) by 322 days.

(21) Appl. No.: 10/644,482

(22) Filed: Aug. 20, 2003

(65) Prior Publication Data

US 2004/0039448 A1  Feb. 26, 2004

Related U.S. Application Data

(62) Division of application No. 09/627,261, filed on Jul. 28, 2000, now Pat. No. 6,610,093.

(51) Int. Cl.
*A61F 2/44* (2006.01)

(52) U.S. Cl. .................. 623/17.15; 623/17.14

(58) Field of Classification Search ............ 623/17.12, 623/17.13, 17.14, 17.15, 17.16; 606/61
See application file for complete search history.

(56) References Cited

U.S. PATENT DOCUMENTS

| 4,309,777 | A | 1/1982 | Patil |
| 4,349,921 | A | 9/1982 | Kuntz |
| 4,401,112 | A | 8/1983 | Rezaian |
| 4,605,417 | A | 8/1986 | Fleischauer |
| 4,759,769 | A | 7/1988 | Hedman et al. |
| 5,258,031 | A | 11/1993 | Salib et al. |
| 5,320,644 | A | 6/1994 | Baumgartner |
| 5,674,296 | A | 10/1997 | Bryan et al. .............. 623/17.16 |
| 5,755,796 | A | 5/1998 | Ibo et al. |
| 6,146,421 | A | 11/2000 | Gordon et al. |
| 6,231,609 | B1 | 5/2001 | Mehdizadeh |
| 6,402,785 | B1 | 6/2002 | Zdeblick et al. ......... 623/17.16 |

FOREIGN PATENT DOCUMENTS

DE            2263842 A  *  7/1974

* cited by examiner

*Primary Examiner*—Brian E. Pellegrino
(74) *Attorney, Agent, or Firm*—Jackson Walker, LLP

(57) ABSTRACT

A method and apparatus for stabilizing adjacent vertebrae. Upper and lower interlocking brackets are insertable in a prepared intervertebral space between adjacent vertebrae. The brackets are affixed to the vertebrae at attachment plates. A rib on one side of one bracket interlocks with a rib receiving groove in the other bracket to stabilize the spinal column without eliminated mobility (forward and rearward flexion) of the column. Various embodiments include additional shock absorption features.

5 Claims, 8 Drawing Sheets

METHOD AND APPARATUS FOR STABILIZING ADJACENT VERTEBRAE

This is a divisional application of U.S. patent application Ser. No. 09/627,261, filed Jul. 28, 2000, now U.S. Pat. No. 6,610,093, issued Aug. 26, 2003.

BACKGROUND OF THE INVENTION

The present invention relates to an intervertebral disk stabilizing implant and a method of stabilizing two adjacent vertebrae. More specifically, the present invention relates to upper and lower interlocking brackets which attach to adjacent vertebrae sufficiently to stabilize the vertebrae but allow for some forward flexion and rearward extension of the spine with slight lateral displacement. An alternative embodiment provides for stability of the spinal column, with flexion and extension with spinal shock absorption.

The spine is a flexible structure comprised of thirty-three vertebrae. The vertebrae are separated and cushioned from each other by fibrous cartilage in structures called intervertebral disks. If the spine is injured or becomes diseased, surgical intervention involving removal of one or more of these disks and fusion of the adjacent vertebrae, may be indicated. Such disk injuries can happen in the neck, in the thoracic region and in the lumbar region. The more frequent injuries are in the lower lumbar and in the lower cervical regions.

Treatment of a herniated disk in the neck and in the lumbar region continues to be a challenging field of medicine. The classical treatment for a ruptured disk continues to be removal of the disk from between the vertebrae. By this process of removing the disk, overall spinal instability is increased. This may aggravate the patient to some degree after the operation. Another procedure previously employed is to replace the disk space with a bone graft, bringing about fusion of the vertebrae above and below the disk, eliminating the empty space between the vertebrae and improving stability.

Theoretically a diskectomy with fusion is a satisfactory procedure, though not ideal because the replaced bone does not have the principal functions of the cartilage tissue of the disk. This fusion procedure is technically demanding and has medical complications because of several physiological factors.

It must be remembered that the disk primarily serves as a mechanical cushion while permitting limited mobility. For any replacement system for a disk to be truly effective, it must allow for mobility within the natural limits of the original disk. In other words, the replacement should match appropriate joint rheology (movement behavior). The natural disk allows about 11 degrees of flexion-extension, limited lateral bending of 3 to 5 degrees, and very restricted rotation of about 1 degree.

Various prosthetic devices and implants are disclosed in the art, but all are characterized by compromises to the full functions of a natural disk discussed above. Examples of the prior art include the following U.S. Pat. Nos. 5,893,890; 5,693,100; 5,658,336; 5,653,761; 5,653,762; 5,390,683; 5,171,278; and 5,123,926. The present invention improves upon the state of the art including the inventor's own prior inventions by more closely approximating the natural function of the disk, including extension-flexion, slight lateral bending, and very slight rotation.

SUMMARY OF THE INVENTION

This present invention provides a method and apparatus for providing vertebral stabilization while further providing shock absorption; flexion and extension (mobility); slight lateral bending; and very slight rotation about the spinal column; and, still achieving spinal stability. The vertebral disk stabilizer of the present invention has upper and lower brackets with vertebral attachment plates. Arcuate surfaces on the brackets provide for a structural configuration which conforms to the shape of the intervertebral space. The upper and lower brackets are linked or attached to one another by complimentary ribs and rib receiving grooves or a "ball and socket" linkage. The stabilizer is vertically affixed to the outer cortial surface of adjacent vertebrae by conventional medical fasteners which extend through the bracket plates into the vertebrae bodies.

An independent intervertebral disk member is disposed and retained between the upper and lower brackets. The disc member may be, alternatively: (a) a compressible composition; (b) a metal disk member with a mechanical spring mechanism affixed between the upper and lower brackets; or (c) a combination of compressible material and mechanical spring.

DETAILED DESCRIPTION OF THE PREFERRED EMBODIMENTS

Figure 1:
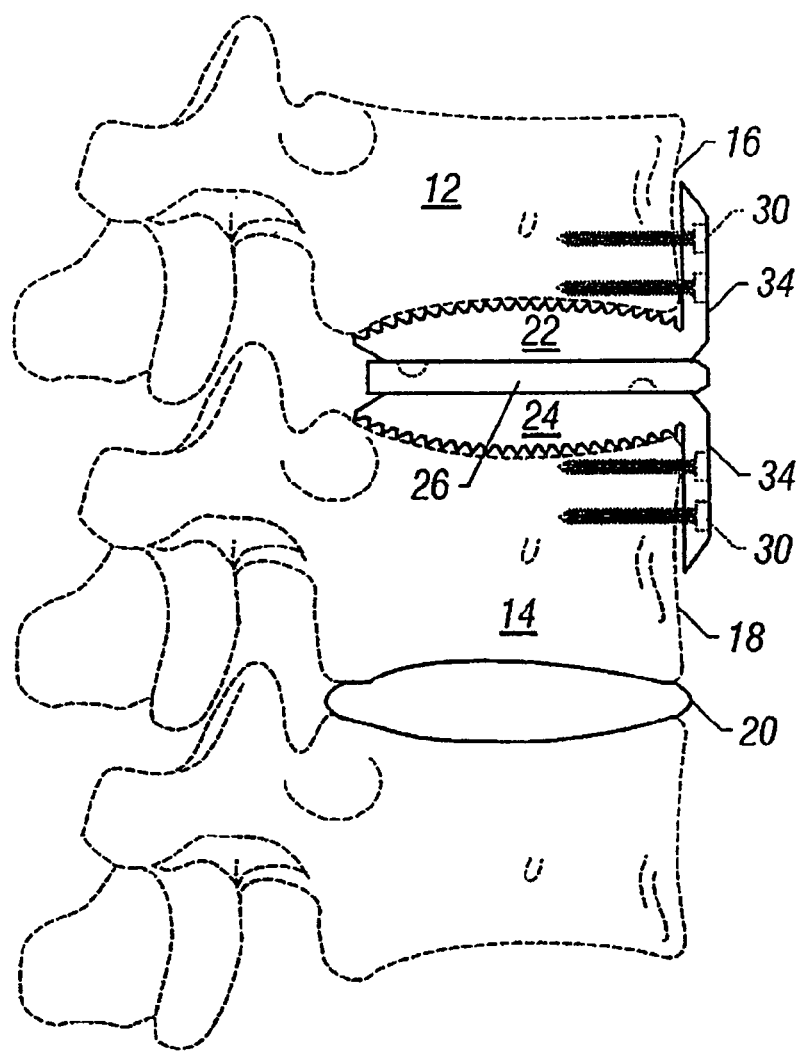
FIG. 1 is a lateral view of a portion of a human spinal column having a preferred embodiment of the vertebral disk stabilizer of the present invention inserted therein.

Referring now to the figures, a first embodiment of a disk stabilizer constructed in accordance with the teachings of the present invention is shown implanted in a human spinal column in FIG. 1. The vertebral disk stabilizer, indicated generally at reference numeral 10, is implanted between the bodies 12 and 14 of adjacent vertebrae 16 and 18, respectively, in the disk space (not numbered) from which a portion of the invertebral disk 20 is removed, i.e., by simple diskectomy and small laminotomy.

Figure 2:
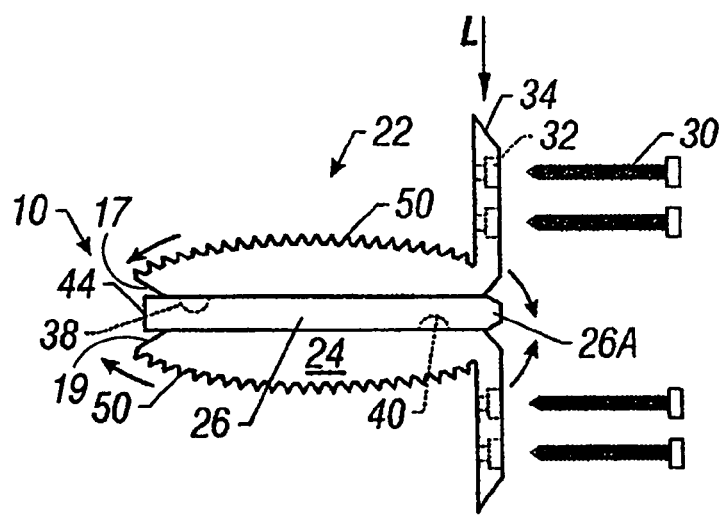
FIG. 2 is a side elevation view of the present invention illustrating the medical fasteners.
Figure 2A:
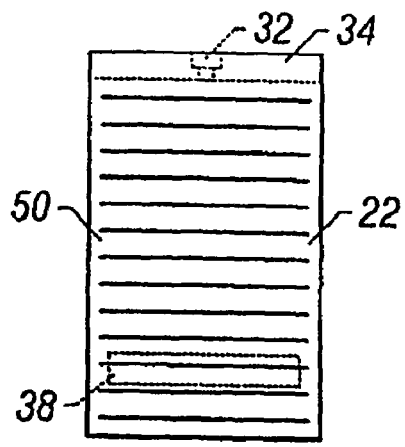
FIG. 2A is a top plan view of the upper bracket of the present invention.

In FIG. 2, the stabilizer 10 is comprised of an upper bracket 22, a lower bracket 24, and an invertebral disk 26. Brackets 22 and 24 may be composed of a strong, thin, non-porous material. Suitable materials for the brackets include carbon fiber, modified carbon, titanium, surgically compatible steel, physiologically inert and/or medically compatible polymers such as urethane or DELRIN® polymers, or any surgical implant or any biologically compatible material.

In the presently preferred embodiment shown, the means for mounting the invention to the spine takes the form of fasteners 30 passing through bores 32 in vertical vertebral attachment plates 34 and into the bodies 12 and 14. The plate ends are tapered for a smooth contour fit to the bodies 12 and 14. The brackets 22 and 24 are linked to the disk 26 by ribs 38 and 40. Ribs 38 and 40 are generally cylindrical protrusions extending transversely partially across the bottom surface of the brackets. Alternatively, one rib could be affixed to the upper bracket 22 and one rib could be attached to the underside of the disk. Thus, the disk rib would be a generally cylindrical protrusion extending transversely partially across the bottom surface of the disk member 26.

Figure 2B:
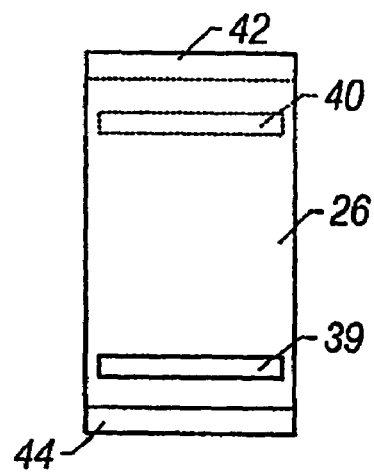
FIG. 2B shows a top plan view of the intervertebral cushion member of the present invention.
Figure 2C:
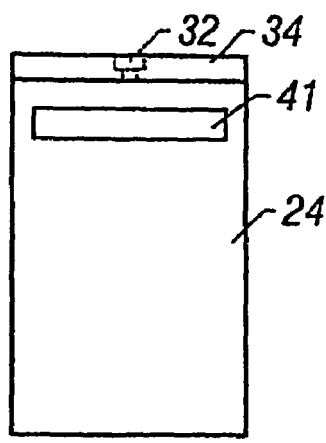
FIG. 2C is a top plan view of the lower bracket of the present invention.

Bracket rib 38 is received and retained in rib receiving groove 39 in the upper surface of disk 26 (FIG. 2B). The rib 38 and groove 39 act as hinge elements or bearing elements and are sized such that the rigid rib 38 is retained into engagement in the groove, but the cylindrical shapes of the rib and groove interlock to resist disengagement. In the alternative where a rib is affixed to the disk, the disk rib would be received and retained in a rib receiving groove in the upper surface of the lower bracket 24.

It is important to understand that the size of effective diameter $d_1$ of a rib 38 or 40 is less than the size or effective diameter $d_2$ of the grooves 39 or 41. This allows for movement of the rib within the groove, but not so much movement as to result in vertebral instability. As will be seen below the groove depth must be sufficient to allow the rib to move vertically in a cushioning or shock absorbing mode of the device 10.

The intervertebral disk 26 may be composed of any number of compressible physiologically inert and/or medically compatible polymers. Again, only by way of example and not as a limitation, the disk could be made of urethane or a DELRIN® polymer. The purpose of the compressible composition is to provide shock absorption between the interlocked brackets 22 and 24. Later it will be shown that mechanical springs may be substituted for the compressible disk composition. In such a case the disk may be constructed by carbon fiber, modified carbon, titanium, surgically compatible steel, or any other rigid material acceptable in such operations.

It should be noted that the outer ends 42 and 44 of disk 26 may be chamfered to allow flexion and extension of the spine through movement of the stabilizer forwardly and rearwardly (shown by arrows in FIG. 2). The desired range of flexion and extension is adjusted by the angle of the chamfer, as the patient bends or leans forward or backwards.

As may be seen in FIGS. 1, 2, 3, and 4, the disk ends 42 and 44 may be chamfered at both ends, one end, or no end. Where flexion and extension require, the bracket ends 17 and 19 maybe chamfered and upon rotation the disk 26 will halt the degree of rotation as will be understood by on skilled in the art. For example, FIG. 2 shows bracket ends 17 and 19 chamfered and disk end 44 squared off. Again, the arrows in FIG. 2 illustrate that flexion and extension are available with the present invention. FIG. 2 further shows that when the present stabilizer 10 is assembled the vertical plates 34 align substantially along the same longitudinal axis L.

Figure 3:
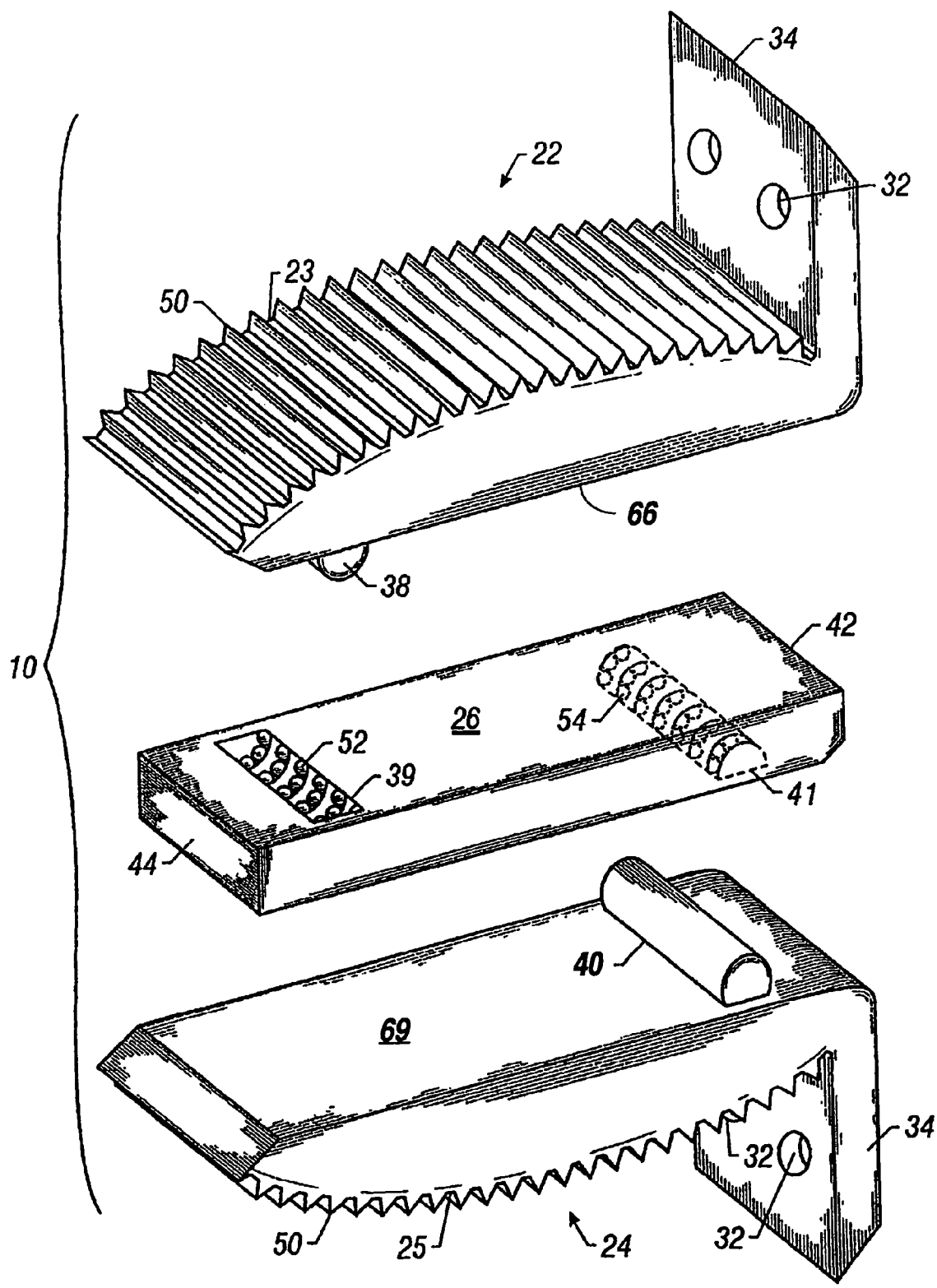
FIG. 3 illustrates an exploded perspective view of one embodiment of the present invention.

In more detail, now referring to FIG. 3, it may be seen that the top arcuate side 23 of upper bracket 22 and the bottom arcuate side 25 of lower bracket 24 are roughened or textured. These arcuate sides 23 and 25 of stabilizer 10 are provided with a plurality of teeth or ridges 505 for biting or gripping into the adjacent vertebrae 16 and 18. Those skilled in the art who have the benefit of this disclosure will recognize the sides 23 and 25 of the stabilizer 10 need not define a true arch which is symmetrical. It will also be recognized that the sides 23 and 25 need not be provided with the serrations 50 to bite into the vertebrae. This biting function can also be accomplished by providing the sides 23 and 25 with multiple steps formed in right angles along sides 23 and 25 or by simply knurling the surfaces of these sides.

As may be seen in FIG. 3, the disk member 26 has only one interlocking member 40 on the rear end 44 on the disk member and only one interlocking member 39 on the front end 42 of the disk member.

Another feature of the present invention illustrated in FIG. 3 is the incorporation of bearing surfaces 52 and 54 in disk member rib receiving grooves 39 and 41. These surfaces are intended to reduce friction and extend the life of the parts. It should be understood that low friction surface materials may be substituted for any type of mechanical bearing.

Figure 4:
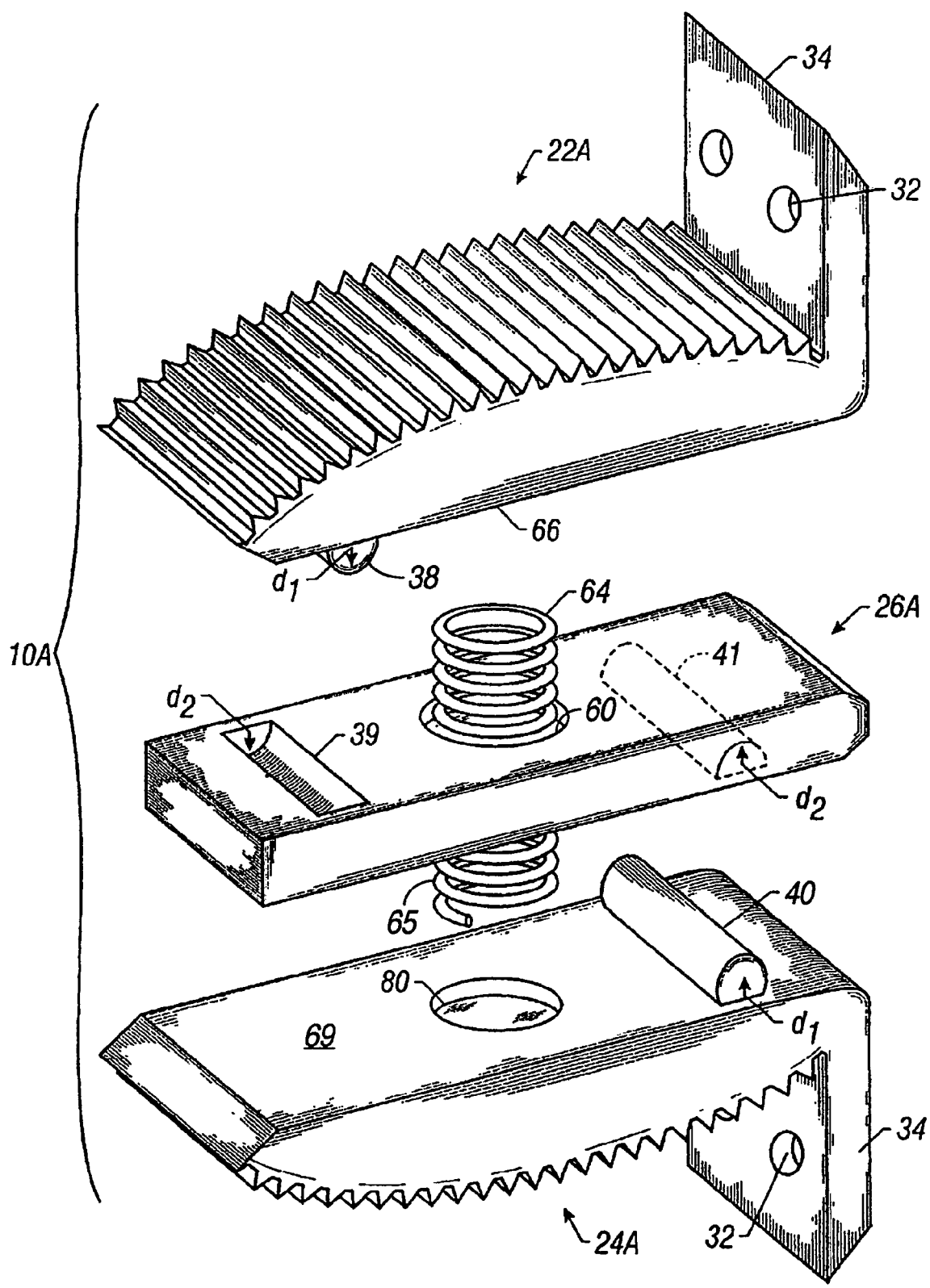
FIG. 4 illustrates an exploded perspective view of another embodiment of the present invention.

An alternative preferred embodiment 10A is illustrated in the exploded perspective view of FIG. 4. In most ways stabilizer 10A is identical to stabilizer 10 except that a mechanical shock absorption mechanism is provided. Disk 26A is provided with two central depressions 60 of sufficient depth and diameter to allow compression springs 64 and 65 to be fitted and retained in depressions 60 (the second depression is on the underside of the disk 26A in FIG. 4). Spring 65 may be attached to bottom surface 69 of the lower bracket 24A in complimentary depression 80. Spring 64 may likewise be attached to the bottom surface 66 of upper bracket 22A. Springs 64 and 65 thus result in a means for varying the degree of shock absorption which may be achieved by the stabilizer 10A.

Figure 4A:
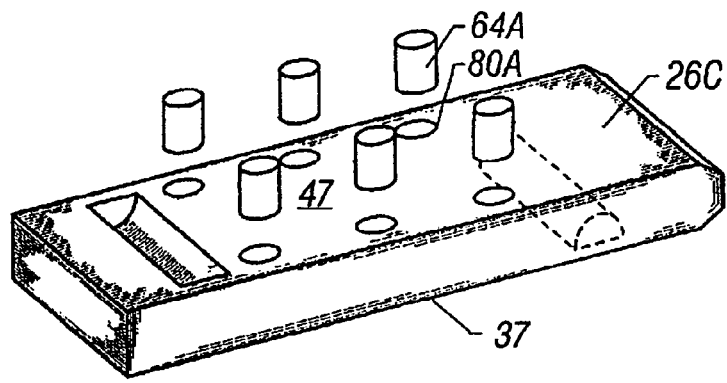
FIG. 4A illustrates an exploded perspective view of an alternative disk of the present invention.
Figure 4B:
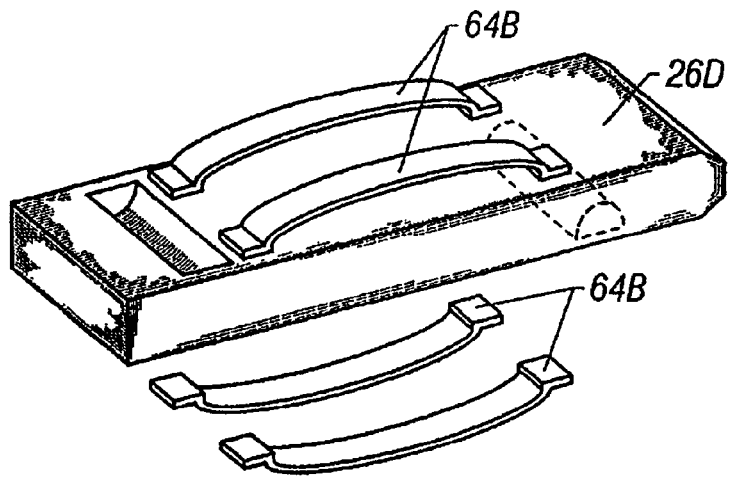
FIG. 4B illustrates an exploded perspective view of yet another disk of the present invention.
Figure 4C:
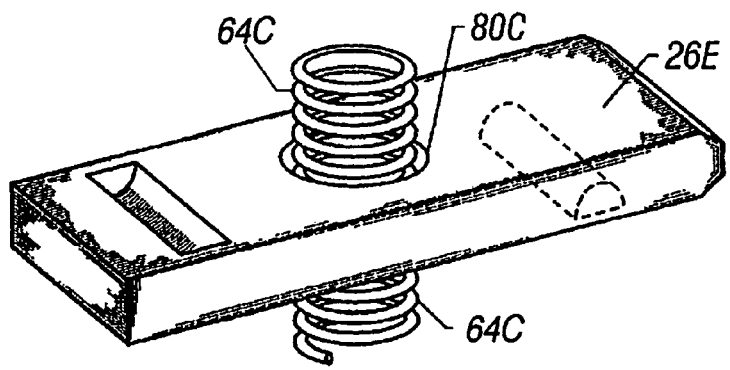
FIG. 4C illustrates an exploded perspective view of an additional disk of the present invention.

FIGS. 4A–4C illustrate alternative disk arrangements available to provide for shock absorption. In FIG. 4A, disk 26C is provided with a multiplicity of depressions 80A along its top surface 47 (and, if desired, bottom surface 37). The depressions are sized to accept and retain compression pillars 64A. By varying the composition and quantity of pillars the physician is able to control the compressive force absorption in each stabilizer. Further, the pillars will allow for a slight degree of lateral vertebral movement. However, the relationship between the diameters $d_1$ and $d_2$ of the ribs and grooves, respectively, controls the total amount of movement available in any embodiment.

FIG. 4B illustrates the utilization of leaf-type springs 64B on this disk embodiment 26D. Further, a unitary spring, a single pillar, or a combination may be used. FIG. 4C shows compression element 64C passes through the disk member 26E through opening 80C and is attachable to the upper and lower brackets, as would be readily understood by one skilled in the art.

Again, it should be understood that any combination of compressible materials and mechanical springs may be employed to absorb shock in the present invention The disk could be metal with compressible pillars; it could be a compressible composition with compressible pillars; or it could be a compressible composition with metal springs.

Figure 5:
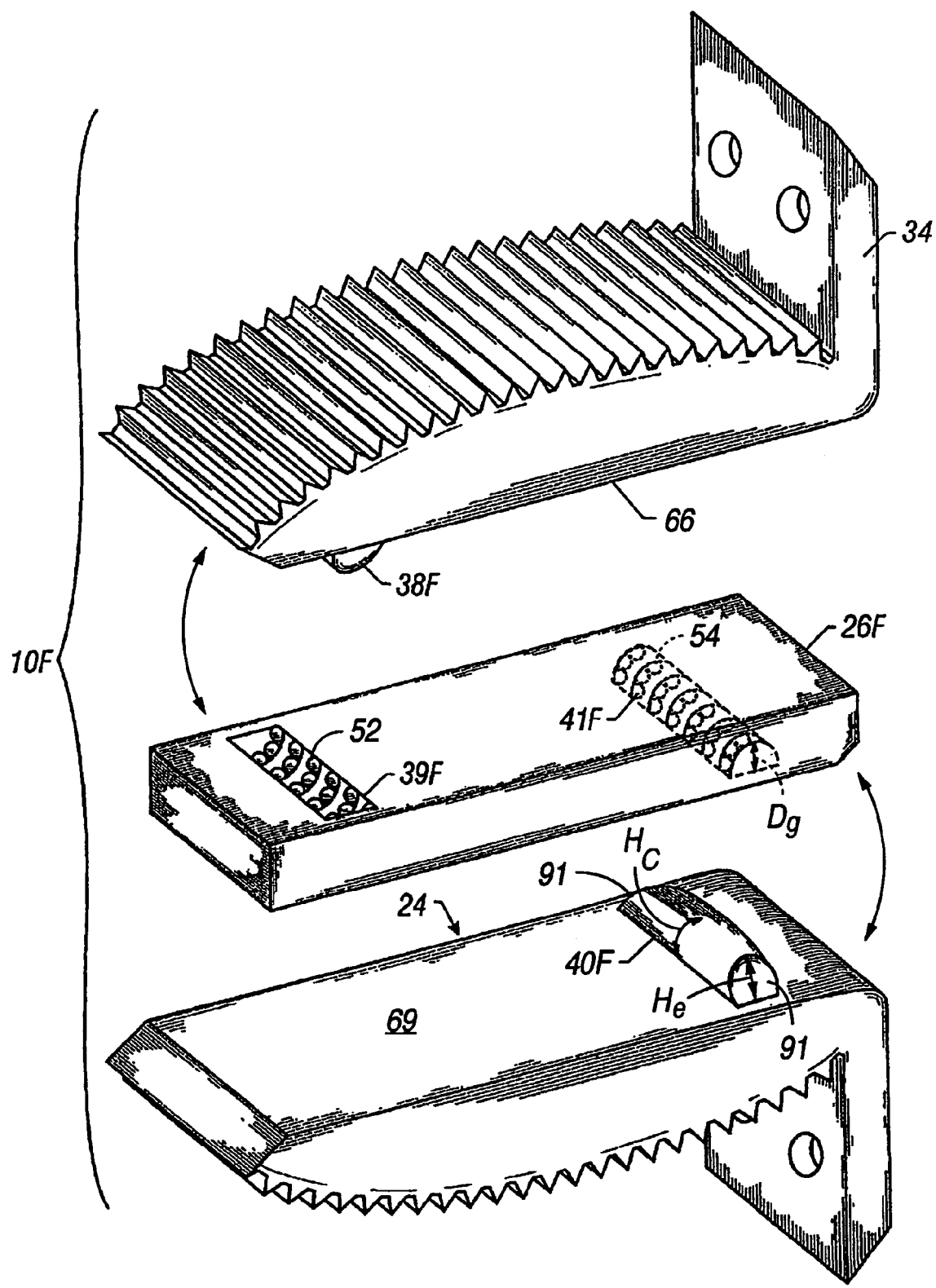
FIG. 5 illustrates an exploded perspective of an embodiment of the present invention with an arcuate rib having inwardly slanting side walls.

Turning to FIG. 5, another embodiment of the present invention 10F may be seen. The key distinction of this embodiment relates to the interlocking ribs 38F and 40F. The central height $H_c$ of the ribs on the bottom side 69 of bracket 24 is greater than the end height $H_e$ of the inwardly slanting side walls 91. The grooves 39F and 41F in disk 26F have depths $D_g$ which are greater than the central height $H_c$. This arrangement, in coordination with the slanting walls 91, allows for the brackets (attached to the vertebrae) to flex, extend, and move laterally with a very slight twisting operation. At the same time, the spinal column is stabilized. As may be seen in F*ig*. 5, the grooves 39F and 41 F may be fitted with roller bearings 52 and 54 to reduce frictional forces as previously discussed with FIG. 3

Figure 6:
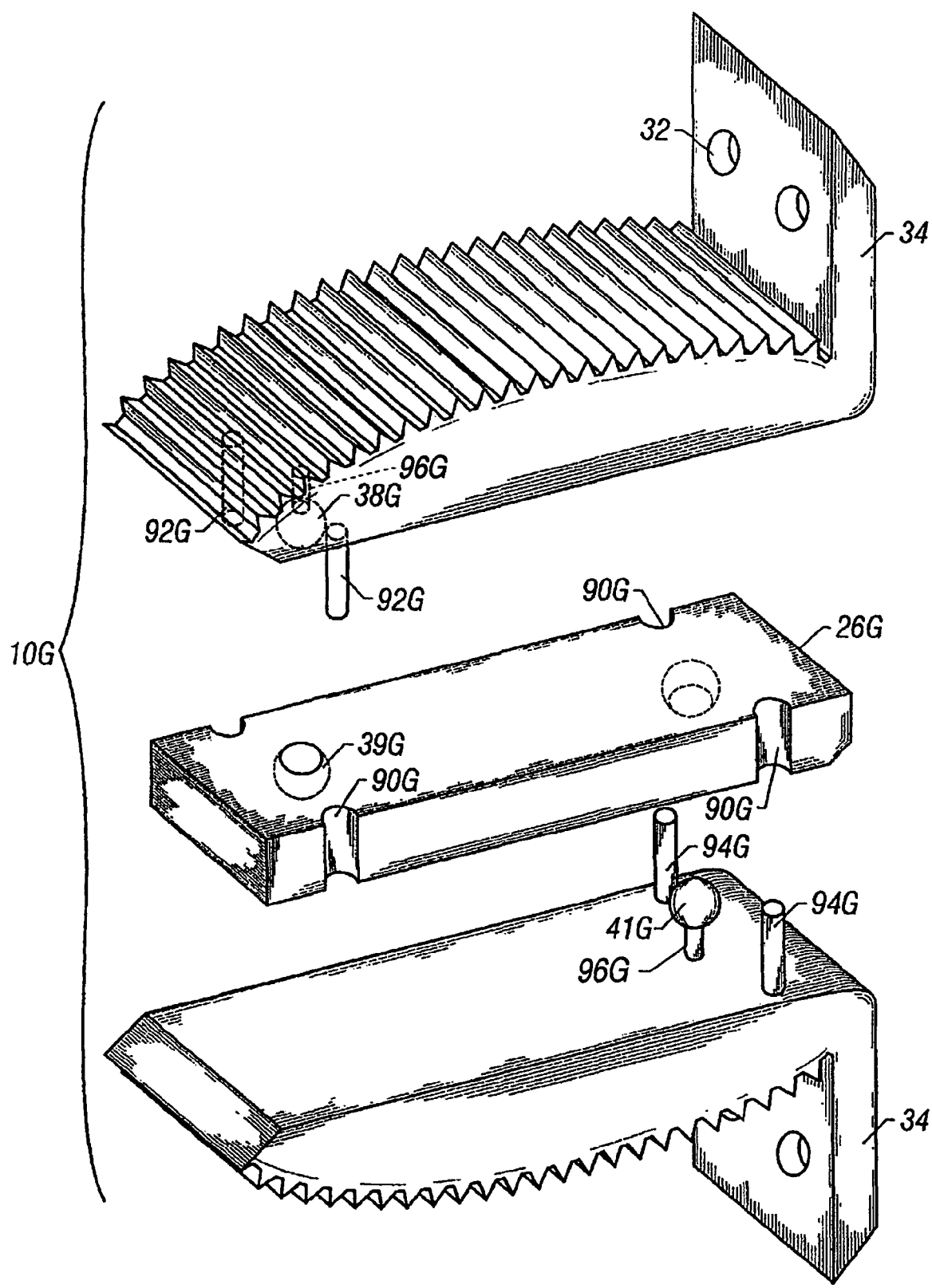
FIG. 6 illustrates an exploded perspective of an embodiment of the present invention with a "ball and socket" linkage.

The embodiment 10G of FIG. 6 utilizes a unique ball and socket linking arrangement. The brackets are provided with a ball 41G at the end of a neck 96G attached to the underside of the bracket. Also attached to the underside are rigid stop pegs 92G and 94G. The pegs 92G and 94G cooperate with stop notches 90G in the invertebral disk 26G to limit excessive lateral motion and rotation of the elements of the device 10G. The pegs 94G have diameters smaller than the diameters of the notches and generally do not contact the notches except when the lateral motion or rotation becomes excessive.

The balls 41G cooperate with the sockets 38G to both receive and retain the interlocking relationship of the separate elements of the invention. The socket has a greater diameter than the ball. The socket wraps over half of the ball diameter to keep the ball from being dislocated during flexion/extension of the spine.

Figure 6A:
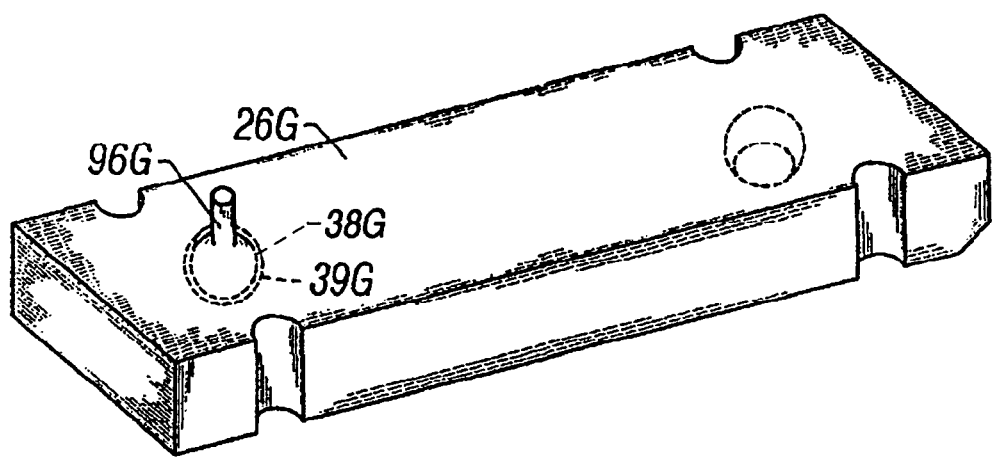
FIG. 6A illustrates in detail the intervertebral disk of one embodiment of the present invention which utilizes the "ball and socket" linkage.

FIG. 6A shows how the ball 38G at the end of neck 96G extends downwardly from the upper bracket into and is retained in the socket 39G in the disk 26G.

It should be understood that the tolerances of the interlocking and cooperating parts are intended to allow for the normal range of movements discussed above. Thus the target range of flexion/extension is 9–12 degrees, lateral bending in the range of 3 to 5 degrees, and a very slight 0.5–1.5 degrees rotation of adjacent joined vertebrae.

Figure 7:
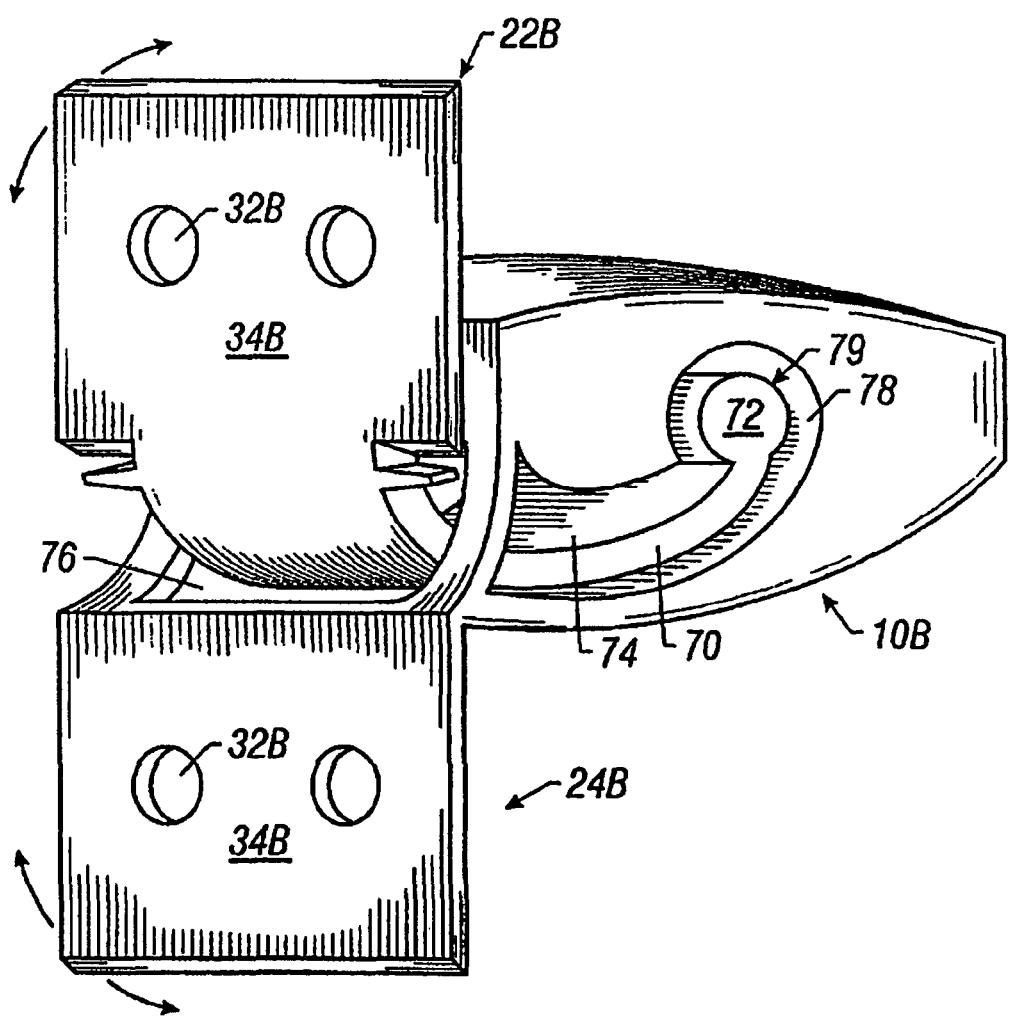
FIG. 7 shows a partial cutaway perspective view of yet another embodiment of the present invention.

Yet another embodiment of the present invention 10B is shown in FIG. 7. Upper bracket 22B has a vertical vertebral attachment plate 34B with bores 32B for receiving fasteners to attach the stabilizer 10B to the first vertebrae body 12. A linking hook 70 is attached to the plate and is arcuated. A rib 72 is formed in the top side 74 of the hook 70. Lower bracket 24B also has a vertical disk attachment plate 34B with bores 32B. An opening 76 is formed in the lower bracket 24B to receive and retain the linking hook 70. An interlocking arcuate cavity 78 is also formed in lower bracket 24B. A rib receiving groove 79 allows the flexion (shown in arrows in FIG. 5) of the stabilizer 10B. There is sufficient "play" or clearances between the hook 70 and rib 72 within the rib receiving groove 79 to maintain stability but allow for limited mobility (flexion).

In each embodiment of the present invention the separate parts are sized to facilitate insertion within the intervertebral space created and sustained between adjacent vertebrae during the medical insertion procedure.

It is anticipated that the stabilizer 10 of the present invention will be fully assembled prior to insertion into the intervetebral space. Thus, by varying the compressive force mechanism and the size of the brackets and disk, the physician will be able to utilize the present invention with any number of different size patents.

The use of the stabilizer 10 of the present invention in, for instance, a method of intervertebral disk stabilization is illustrated in FIG. 1. Surgery is performed as a simply diskectomy and the intervertebral disk 20 is exposed. The natural deteriorated disk material is removed and any nerve root compression is corrected. Any ligament, muscle, or cartilage covering the vertebrae are moved or removed until the surface of the bodies 12 and 14 of adjacent vertebrae 16 and 18, respectively, are exposed above and below the disk space.

Using spreaders the vertebrae 16 and 18 are distracted to open the disk space sufficient to inset the stabilizer.

A stabilizer 10 having a height and width selected to fit the disk space is then mounted to an applicator (not shown) as is well known in the art. The appropriate sized stabilizer 10 is then inverted into the disk space with the stabilizer oriented so that the upper convex side 23 of bracket 22 and bottom convex side 25 of bracket 24 engage the bodies 12 and 14 of adjacent vertebrae 16 and 18, respectively. The vertical attachment plates or plates 34 are vertically aligned with the vertebrae. Fasteners 30 are then passed through bores 32 thereby securing the upper and lower brackets to the spinal column.

Although the invention has been described with reference to a specific embodiment, this description is not meant to be construed in a limiting sense. On the contrary, various modifications of the disclosed embodiments will become apparent to those skilled in the art upon reference to the description of the invention. It is therefore contemplated that the appended claims will cover such modifications, alternatives, and equivalents that fall within the true spirit and scope of the invention.

The invention claimed is:

1. A vertebral disk stabilizer for allowing adjacent vertebrae to flex forwardly and extend rearwardly comprising:
    a first vertebral bracket having a vertebrae contact side, an opposing interlocking side, a front end, a rear end, and an attachment plate for attachment to a first of said adjacent vertebrae;
    a second vertebral bracket having a vertebrae contact side, an opposing interlocking side, a front end, a rear end, and an attachment plate for attachment to a second of said adjacent vertebrae; and
    a separate intervertebral disk member having a front end and a rear end and only one interlocking member on said front end of said disk member interlocking said interlocking side of said first vertebral bracket at said front end of said first vertebral bracket with said front end of said disk member and only one interlocking member on said rear end of said disk member interlocking said interlocking side of said second vertebral bracket at said rear end of said second vertebral bracket with said rear end of said disk member.

2. The stabilizer of claim 1 further comprising:
    a supplemental compression member disposed between said interlocking side of each of said first and said second vertebral brackets.

3. The stabilizer of claim 2 wherein said supplemental compression member is selected from the group consisting of a compression spring, a leaf spring, and a compression plug.

4. The stabilizer of claim 1 wherein said interlocking member on each of said front end and said rear end of said disk member is selected from the group consisting of a rib, a groove, a ball, a socket, and a bearing element.

5. The stabilizer of claim 4 wherein said interlocking member on said disk member cooperates with a complimentary interlocking member on said front end and said rear end of each of said vertebral brackets, said complimentary interlocking member is selected from the group consisting of a rib, a groove, a ball, a pocket, and a bearing element.

* * * * *